United States Patent
Kato et al.

(10) Patent No.: US 11,424,129 B2
(45) Date of Patent: Aug. 23, 2022

(54) METHOD OF ETCHING BORON-DOPED P-TYPE SILICON WAFER, METHOD OF EVALUATING METAL CONTAMINATION OF BORON-DOPED P-TYPE SILICON WAFER AND METHOD OF MANUFACTURING BORON-DOPED P-TYPE SILICON WAFER

(71) Applicant: SUMCO CORPORATION, Tokyo (JP)

(72) Inventors: Hirokazu Kato, Nagasaki (JP); Takafumi Yamashita, Saga (JP)

(73) Assignee: SUMCO CORPORATION, Tokyo (JP)

( * ) Notice: Subject to any disclaimer, the term of this patent is extended or adjusted under 35 U.S.C. 154(b) by 166 days.

(21) Appl. No.: 16/982,233

(22) PCT Filed: Dec. 12, 2018

(86) PCT No.: PCT/JP2018/045621
§ 371 (c)(1),
(2) Date: Sep. 18, 2020

(87) PCT Pub. No.: WO2019/181104
PCT Pub. Date: Sep. 26, 2019

(65) Prior Publication Data
US 2021/0028023 A1    Jan. 28, 2021

(30) Foreign Application Priority Data
Mar. 22, 2018    (JP) .............................. JP2018-054306

(51) Int. Cl.
*H01L 21/3065*    (2006.01)
*H01L 21/66*    (2006.01)

(52) U.S. Cl.
CPC .......... *H01L 21/3065* (2013.01); *H01L 22/20* (2013.01)

(58) Field of Classification Search
None
See application file for complete search history.

(56) References Cited

U.S. PATENT DOCUMENTS

| 5,423,944 | A | 6/1995 | Wong |
| 5,994,238 | A | 11/1999 | Park |
| 2003/0073240 | A1 | 4/2003 | Mizuno |
| 2021/0028023 | A1* | 1/2021 | Kato ....................... H01L 22/12 |
| 2021/0118694 | A1* | 4/2021 | Zhang ................. H01L 21/3065 |

FOREIGN PATENT DOCUMENTS

| JP | 6-168922 | 6/1994 |
| JP | 9-190999 | 7/1997 |
| JP | 2001-208743 | 8/2001 |
| JP | 2011-95016 | 5/2011 |
| JP | 2015-52476 | 3/2015 |
| WO | 2014/129246 | 8/2014 |
| WO | 2017/149833 | 9/2017 |

OTHER PUBLICATIONS

Official Communication issued in International Bureau of WIPO Patent Application No. PCT/JP2018/045621, dated Feb. 5, 2019.
IPRP for PCT/JP2018/045621, dated Oct. 1, 2020 (w/ translation).

* cited by examiner

*Primary Examiner* — Jack S Chen
(74) *Attorney, Agent, or Firm* — Greenblum & Bernstein, P.L.C.

(57) ABSTRACT

The method of etching a boron-doped p-type silicon wafer includes preparing an etching gas by introducing an ozone-containing gas and hydrofluoric acid mist into a chamber and mixing them; and performing gas phase decomposition of a surface layer area of a boron-doped p-type silicon wafer with a resistivity of 0.016 Ωcm or less by bringing the etching gas into contact with a surface of the boron-doped p-type silicon wafer; and further includes introducing the ozone-containing gas into the chamber at a flow rate of 3,000 sccm or more; and preparing the hydrofluoric acid mist by atomizing hydrofluoric acid with a hydrofluoric acid concentration of 41 mass % or more.

6 Claims, No Drawings

METHOD OF ETCHING BORON-DOPED P-TYPE SILICON WAFER, METHOD OF EVALUATING METAL CONTAMINATION OF BORON-DOPED P-TYPE SILICON WAFER AND METHOD OF MANUFACTURING BORON-DOPED P-TYPE SILICON WAFER

CROSS-REFERENCE TO RELATED APPLICATIONS

This application claims the benefit of priority to Japanese Patent Application No. 2018-054306 filed on Mar. 22, 2018, which is expressly incorporated herein by reference in its entirety.

TECHNICAL FIELD

The present invention relates to a method of etching a boron-doped p-type silicon wafer, a method of evaluating metal contamination of a boron-doped p-type silicon wafer and a method of manufacturing a boron-doped p-type silicon wafer

BACKGROUND ART

Regarding semiconductor devices, it is known that metal impurity contamination on the surface of a semiconductor substrate affects device characteristics such as leakage failure, oxide film breakdown voltage failure, and reduced lifetime. In addition, it has been reported that not only metal impurity contamination on the surface of a semiconductor substrate but also metal impurity contamination in a surface layer area of the semiconductor substrate, on which a device structure such as a shallow trench, a source, and a drain are formed, affect device characteristics.

Regarding a method of evaluating metal contamination on the surface and in a surface layer area of a silicon wafer which is widely used as a semiconductor substrate, a method in which a surface layer area of a silicon wafer is decomposed, a recovery liquid is scanned on the surface of the silicon wafer after decomposition, the decomposed residues are recovered in the recovery liquid, and metal components in the recovery liquid are analyzed may be exemplified. Regarding a method of decomposing a surface layer area of a silicon wafer for this analysis, a method in which an etching gas is brought into contact with a surface of a silicon wafer, and the surface layer area is gas-phase decomposed and etched (gas phase etching) is known (for example, refer to Documents 1 and 2, which are expressly incorporated herein by reference in their entirety).

Document 1: WO2014/129246

Document 2: Japanese Patent Application Publication No. 2015-52476

SUMMARY OF THE INVENTION

The conductivity type of the silicon wafer is determined according to a dopant. For example, a p-type silicon wafer can be obtained using boron (B) as a dopant. In addition, the resistivity of the boron-doped p-type silicon wafer is controlled according to the concentration of boron.

In recent years, there has been a demand for boron-doped p-type silicon wafers with various resistivities and the need for low resistance boron-doped silicon wafers has been increasing. However, the inventors conducted studies and found that, when the resistivity of a boron-doped p-type silicon wafer is low, even if a recovery liquid is recovered after the recovery liquid is scanned on the surface of the wafer after gas phase etching, a recovery rate of the recovery liquid tends to decrease. When the recovery rate of the recovery liquid from the surface of the wafer decreases, the recovery rate of metal components from the surface of the wafer after gas phase decomposition decreases as a result. Metal components present in the decomposed surface layer area (the surface and the inside in the surface layer area) remain on the surface of the wafer after gas phase etching. Therefore, if these metal components are recovered and analyzed, it is possible to evaluate the presence or degree of metal contamination of the surface layer area of an evaluation target wafer. However, when the recovery rate of metal components from the surface of the wafer after gas phase etching is low, even if the metal components in the recovery liquid are analyzed, the analysis results may not sufficiently correspond to the presence or degree of metal contamination on the surface and in the surface layer area of the evaluation target wafer, and the reliability of evaluation decreases.

One aspect of the present invention provides for a gas phase etching method of a low-resistance boron-doped p-type silicon wafer through which it is possible to recover a recovery liquid scanned on a surface of the wafer after etching at a high recovery rate.

One aspect of the present invention relates to:

a method of etching a boron-doped p-type silicon wafer, including:

preparing an etching gas by introducing an ozone-containing gas and hydrofluoric acid mist into a chamber and mixing them; and performing gas phase decomposition of a surface layer area of the boron-doped p-type silicon wafer with the resistivity of 0.016 Ωcm or less by bringing the etching gas into contact with the surface of the boron-doped p-type silicon wafer; and further including:

introducing the ozone-containing gas into the chamber at a flow rate of 3,000 sccm or more; and preparing the hydrofluoric acid mist by atomizing hydrofluoric acid with a hydrofluoric acid concentration of 41 mass % or more.

In an embodiment, the ozone concentration of the above ozone-containing gas can be in a range of 0.5 mass % to 3.5 mass %.

In an embodiment, the above etching method can include preparing the hydrofluoric acid mist by atomizing hydrofluoric acid with a carrier gas at a flow rate of 700 sccm or more and 1,300 sccm or less.

In an embodiment, the above etching method can include introducing the carrier gas into a chamber separate from the chamber into which the ozone-containing gas and the hydrofluoric acid mist are introduced and performing the above gas phase decomposition in the separate chamber.

Another aspect of the present invention relates to:

a method of evaluating metal contamination of a boron-doped p-type silicon wafer, in which the resistivity of the boron-doped p-type silicon wafer that is an evaluation target is 0.016 Ωm or less, the method including:

etching the boron-doped p-type silicon wafer according to the above etching method;

scanning a recovery liquid on the surface of the boron-doped p-type silicon wafer after etching;

recovering the scanned recovery liquid from the surface of the boron-doped p-type silicon wafer; and analyzing metal components in the recovery liquid that are recovered.

Another aspect of the present invention relates to:

a method of manufacturing a boron-doped p-type silicon wafer, including: manufacturing the boron-doped p-type silicon wafer for process evaluation with the resistivity of 0.016 Ωcm or less in a process of manufacturing the boron-doped p-type silicon wafer;

evaluating the presence, the degree, or the presence and the degree of metal contamination in the boron-doped p-type silicon wafer for process evaluation according to the above metal contamination evaluation method; and determining the necessity of process management of the manufacturing process based on a result of evaluation; and manufacturing a boron-doped p-type silicon wafer for shipping as a product after process management when it is determined that process management is necessary or without process management when it is determined that process management is unnecessary.

According to one aspect of the present invention, after a low-resistance boron-doped p-type silicon wafer with the resistivity of 0.016 Ωcm or less is subjected to gas phase etching, it is possible to recover the recovery liquid scanned on the surface of the wafer after etching at a high recovery rate. Thereby, it is possible to recover metal components from the surface of the wafer after etching at a high recovery rate.

DESCRIPTION OF EMBODIMENTS

[Etching Method]

One aspect of the present invention relates to a method of etching a boron-doped p-type silicon wafer which includes preparing an etching gas by introducing an ozone-containing gas and hydrofluoric acid mist into a chamber and mixing them, and performing gas phase decomposition of a surface layer area of the boron-doped p-type silicon wafer with the resistivity of 0.016 Ωcm or less by bringing the etching gas into contact with the surface of the boron-doped p-type silicon wafer, and further includes introducing the ozone-containing gas into the chamber at a flow rate of 3,000 sccm or more, and preparing the hydrofluoric acid mist by atomizing hydrofluoric acid with a hydrofluoric acid concentration of 41 mass % or more.

Hereinafter, the Above Etching Method Will be Described in More Detail.

<Etching Target>

An etching target in the above etching method is a boron-doped p-type silicon wafer with the resistivity of 0.016 Ωcm or less. Hereinafter, such a low-resistance boron-doped p-type silicon wafer will be simply referred to as "silicon wafer" or "wafer".

Through their studies, the present inventors confirmed a phenomenon in which, regarding a low-resistance boron-doped p-type silicon wafer, specifically, a low-resistance boron-doped p-type silicon wafer with the resistivity of 0.016 Ωcm or less, the recovery rate of a recovery liquid scanned on the surface of the wafer after gas phase etching was low. In contrast, according to the etching method of one aspect of the present invention, which will be described below in detail, it is possible to recover a recovery liquid scanned on the surface of a low-resistance boron-doped p-type silicon wafer with the resistivity of 0.016 Ωcm or less after etching at a high recovery rate. In this regard, the inventors have determined that a low-resistance boron-doped p-type silicon wafer with the resistivity of 0.016 Ωcm or less has a higher boron concentration than and a different component composition from a boron-doped p-type silicon wafer with a high resistivity, and thus surface roughness tends to occur after etching, and accordingly, a part of the recovery liquid scanned on the surface of the wafer after etching is likely to remain on the surface of the wafer, which causes a decrease in the recovery rate of the recovery liquid. In contrast, the present inventors speculated that, according to the above etching method, it is possible to suppress the occurrence of surface roughness due to etching, which can contribute to improving the recovery rate of the recovery liquid. The resistivity of the wafer of the etching target is 0.016 Ωcm or less, or can be 0.015 Ωcm or less or 0.012 Ωcm or less. In addition, the resistivity of the wafer of the etching target can be, for example, 0.005 Ωcm or more, 0.010 Ωcm or more, or 0.011 Ωcm or more, but may be lower than these exemplified lower limits. The resistivity can be determined by a method known as a method of measuring a resistivity of a semiconductor wafer.

Etching of the silicon wafer can be performed by bringing an etching gas into contact with a surface of the wafer that is an etching target and performing gas phase decomposition of a surface layer area of the wafer. The surface layer area subjected to gas phase decomposition is a partial area extending from the surface of the silicon wafer in a depth direction. In general evaluation of metal contamination of a silicon wafer, an area with a thickness of about 0.02 μm to about 10 μm from the surface of the silicon wafer is an area to be analyzed in many cases. Therefore, in an example, the thickness of the surface layer area to be etched can be about 0.02 μm to about 10 μm. However, the thickness of the surface layer area may be outside this range, and set according to the purpose of etching. In addition, the thickness of the silicon wafer that is an etching target can be, for example, in a range of 500 μm to 1,200 μm, but is not limited to this range.

<Preparation of Etching Gas>

The etching gas which will be brought into contact with the surface of the silicon wafer that is the etching target is prepared by introducing an ozone-containing gas and hydrofluoric acid mist into a chamber (an etching gas preparation chamber) and mixing them. The etching gas preparation chamber may be the same chamber as a chamber in which gas phase decomposition is performed (a gas phase decomposition chamber) or another chamber. In an embodiment in which the etching gas preparation chamber is a chamber separate from the gas phase decomposition chamber, chambers having various known configurations in which an etching gas can be supplied from the etching gas preparation chamber to the gas phase decomposition chamber can be used. As an example in which an etching gas preparation chamber and a gas phase decomposition chamber communicate with each other in an air-permeable manner, an etching device described in Document 1 (WO2014/129246; refer to FIG. 1, FIG. 2, and the like in this document) may be exemplified. However, the chamber used in the above etching method is not limited to that of the etching device described in Document 1.

In the above etching method, in order to prepare the etching gas, the ozone-containing gas and the hydrofluoric acid mist are introduced into the etching gas preparation chamber. The ozone-containing gas and the hydrofluoric acid mist are preferably introduced continuously or intermittently in a continual manner during gas phase decomposition of the surface layer area of the silicon wafer, and more preferably introduced continuously in a continual manner. In addition, the chamber in which gas phase decomposition is performed preferably includes a discharge unit that can discharge at least some of the etching gas in contact with the surface of the silicon wafer to the outside of the chamber.

Hereinafter, the introduction of the ozone-containing gas and the introduction of the hydrofluoric acid mist into the etching gas preparation chamber will be described in more detail.

(Introduction of Ozone-Containing Gas)

The ozone-containing gas is introduced into the etching gas preparation chamber at a flow rate of 3,000 sccm or more. The unit "sccm" regarding a flow rate is an abbreviation for "standard cc/min" and means a flow rate (cc/min) in an environment under atmospheric pressure (1,013 hPa) and at a temperature of 0° C. in the present invention and this specification. An environment in which etching is performed may be an environment other than the above-mentioned pressure and temperature environment, and in this case, the ozone-containing gas is introduced into the etching gas preparation chamber at a flow rate of 3,000 sccm or more in terms of the flow rate in the above mentioned pressure and temperature environment. Introduction of the ozone-containing gas into the etching gas preparation chamber at the flow rate of 3,000 sccm or more contributes to improving the recovery rate of the recovery liquid scanned on the surface of the wafer after etching. On the other hand, in consideration of ease of preparation of the ozone-containing gas, the flow rate is preferably 5,000 sccm or less and more preferably 4,000 sccm or less. In addition, in order to increase a reaction rate of a gas phase decomposition reaction, the ozone concentration of the ozone-containing gas is preferably 0.5 mass % or more and more preferably 0.7 mass % or more. On the other hand, in consideration of ease of preparation of the ozone-containing gas, the ozone concentration of the ozone-containing gas is preferably 3.5 mass % or less, more preferably 2.0 mass % or less, and still more preferably 1.0 mass % or less. The ozone-containing gas can be prepared by a known method such as a method using dielectric barrier discharge. The ozone-containing gas can be introduced into the etching gas preparation chamber from at least one opening from the etching gas preparation chamber and can also be introduced from two or more openings. When the ozone-containing gas is introduced into the etching gas preparation chamber from two or more openings, a flow rate of the ozone-containing gas into the etching gas preparation chamber means a total flow rate from these two openings. The same applies to introduction of the hydrofluoric acid mist.

(Introduction of Hydrofluoric Acid Mist)

The hydrofluoric acid mist can be prepared by atomizing hydrofluoric acid (an aqueous solution of hydrofluoric acid). Regarding the hydrofluoric acid, hydrofluoric acid with a hydrofluoric acid (HF) concentration of 41 mass % or more is used, which contributes to improving the recovery rate of the recovery liquid scanned on the surface of the wafer after etching. In order to further increase the recovery rate of the recovery liquid, the HF concentration of the hydrofluoric acid is preferably 43 mass % or more. On the other hand, in consideration of ease of preparation or availability, the HF concentration of the hydrofluoric acid is preferably 50 mass % or less.

The hydrofluoric acid can be atomized by an atomization device having a known configuration (generally called a "nebulizer") that can atomize a solution by mixing it with a carrier gas and provide a gas stream containing droplets of the solution. As one example, a negative pressure suction type nebulizer may be exemplified.

Regarding a carrier gas for atomization, one type of an inert gas or a mixture gas of two or more thereof can be used. Specific examples thereof include nitrogen gas, argon gas and the like. A flow rate of the carrier gas is preferably 700 sccm or more in order to efficiently atomize the hydrofluoric acid. On the other hand, in order to increase the concentration of the hydrofluoric acid in the hydrofluoric acid mist, the flow rate of the carrier gas is preferably 1,300 sccm or less.

<Gas Phase Decomposition of Surface Layer Area of Silicon Wafer>

When the etching gas is brought into contact with the surface of the silicon wafer that is an etching target, the surface layer area of the silicon wafer can be subjected to gas phase decomposition. A time for which the etching gas is in contact with the silicon wafer surface (etching time) can be, for example, 0.1 to 4 hours. However, the etching time may be set according to the thickness of the surface layer area which will be subjected to gas phase decomposition, and is not limited to the above range. The temperature in the chamber in which gas phase decomposition is performed can be, for example, about 17° C. to about 29° C.

Metal components contained in the surface layer area (the surface and the inside in the surface layer area) subjected to gas phase decomposition remain on the surface of the silicon wafer after gas phase decomposition. Therefore, when metal components are recovered from the surface of the silicon wafer after gas phase decomposition and analyzed, it is possible to evaluate the presence and/or degree of metal contamination in the surface layer area. However, as described above, regarding the low-resistance boron-doped p-type silicon wafer with the resistivity of 0.016 Ωcm or less, the recovery rate of the recovery liquid from the surface of the wafer after gas phase etching tends to decrease. However, when the recovery rate of the recovery liquid from the surface of the silicon wafer after gas phase decomposition is low, the recovery rate of metal components contained in the surface layer area is reduced as a result, and the reliability of evaluation of metal contamination deteriorates. In contrast, according to the above etching method, regarding the low-resistance boron-doped p-type silicon wafer with the resistivity of 0.016 Ωcm or less, it is possible to recover the recovery liquid scanned on the surface of the silicon wafer after gas phase decomposition at a high recovery rate.

[Metal contamination evaluation method]

One aspect of the present invention relates to a method of evaluating metal contamination of a boron-doped p-type silicon wafer, in which the resistivity of the boron-doped p-type silicon wafer that is an evaluation target is 0.016 Ωcm or less, the method including etching the boron-doped p-type silicon wafer according to the above etching method, scanning a recovery liquid on the surface of the boron-doped p-type silicon wafer after etching, recovering the scanned recovery liquid from the surface of the boron-doped p-type silicon wafer, and analyzing metal components in the recovery liquid.

The boron-doped p-type silicon wafer that is an evaluation target in the above metal contamination evaluation method is a low-resistance boron-doped p-type silicon wafer with the resistivity of 0.016 Ωcm or less. Details of such a wafer are the same as those described above for the silicon wafer that is an etching target in the above etching method. In the above metal contamination evaluation method, the boron-doped p-type silicon wafer that is an evaluation target is etched by the above etching method. Details of the etching method are the same as described above.

Hereinafter, processes after etching will be described in more detail.

<Scanning of Recovery Liquid on Surface of Wafer after Etching>

In the above metal contamination evaluation method, the recovery liquid is scanned on the surface of the silicon wafer that is an evaluation target. Specifically, the surface on which the recovery liquid is scanned is a surface that is exposed when the surface layer area is removed by gas phase decomposition after the etching. Before the recovery liquid is scanned, the silicon wafer can be optionally heated. By this heating, water contained in the etching gas and/or water generated due to the gas phase decomposition reaction can be dried, and easily decomposable substances generated due to the gas phase decomposition reaction can also be removed from the surface of the wafer. The heating temperature is preferably a wafer surface temperature of about 90° C. to about 100° C. The heating method and the heating time are not particularly limited.

Scanning of the recovery liquid on the surface of the wafer can be performed by a method known as a method of recovering metal components using a recovery liquid from the surface of a wafer after gas phase etching. For example, scanning of the recovery liquid can be performed using a recovery liquid scanning nozzle (hereinafter referred to as a "scan nozzle") and moving the nozzle on the surface of the wafer while holding the recovery liquid as droplets at a nozzle tip. Then, when the droplets are sucked from the nozzle, it is possible to recover the recovery liquid scanned on the surface of the wafer. Regarding the recovery liquid scanning nozzle, a nozzle having a known configuration can be used. A moving speed of the nozzle on the surface of the wafer can be, for example, about 2 mm/s to about 3 mm/s. When the recovery liquid scanning nozzle is automatically moved, it is possible to automatically scan the recovery liquid on the surface of the wafer.

Regarding the recovery liquid, a recovery liquid known as a recovery liquid with which metal components are recovered from the surface of a silicon wafer can be used. Examples of such a recovery liquid include pure water, a mixed acid aqueous solution containing hydrofluoric acid and hydrogen peroxide, a mixed acid aqueous solution containing hydrogen peroxide and hydrochloric acid, and a mixed acid aqueous solution containing hydrofluoric acid, hydrogen peroxide, and hydrochloric acid. When a recovery liquid containing an acid component is used, regarding the concentration of the acid component, any known technique can be applied without limitation. In addition, the amount of the recovery liquid used can be, for example, about 700 μl to about 1,000 μl, but is not limited to this range, and may be determined in consideration of the size of the silicon wafer that is an evaluation target and the like.

<Analysis of Metal Components>

Metal components contained in the surface layer area of the silicon wafer removed by etching are incorporated into the recovery liquid. Therefore, when metal components in the recovery liquid are analyzed, qualitative analysis and/or quantitative analysis of metal components contained in the surface layer area of the silicon wafer removed by etching can be performed. The metal components can be analyzed by an analysis device known as a metal component analysis device, for example, through inductively coupled plasma mass spectrometry (ICP-MS), atomic absorption spectrometry (AAS), or the like. The recovery liquid recovered after being scanned on the surface of the silicon wafer can be introduced directly into the analysis device or can be introduced into the analysis device after being diluted or concentrated as necessary. According to the etching method of one aspect of the present invention described above, regarding the low-resistance boron-doped p-type silicon wafer with the resistivity of 0.016 Ωcm or less, it is possible to recover the recovery liquid scanned on the surface of the wafer after etching at a high recovery rate. As a result, it is possible to recover metal components contained in the surface layer area (the surface and the inside in the surface layer area) of the silicon wafer that is an evaluation target at a high recovery rate, and it is possible to evaluate the presence and/or degree of metal contamination of the surface layer area of the silicon wafer that is an evaluation target with high reliability.

The above metal contamination evaluation method can be performed in an automatic evaluation system in which execution of processes and transfer of a wafer between processes are automatically performed. For example, in an evaluation device including an etching unit, a heating unit, a recovery unit, and an analysis unit, loading of a wafer into the etching unit, execution of the etching method in the etching unit, loading of the etched wafer into the heating unit, heating and drying of the wafer in the heating unit, loading of the wafer into the recovery unit, supply, scan and recovery of a recovery liquid on the surface of the wafer in the recovery unit, and analysis of metal components in the recovery liquid in the analysis unit can be automatically performed. For example, execution of processes and transfer of a wafer in the above respective units can be programmed, a program can be executed by a control unit, and thus all of the processes can be automatically performed (fully automatic evaluation). When the recovery rate of the recovery liquid from the surface of the wafer after etching is low, it may be necessary to manually recover the recovery liquid remaining on the surface of the wafer again. In contrast, according to the etching method of one aspect of the present invention described above, it is possible to recover the recovery liquid scanned on the etched surface of the low-resistance boron-doped p-type silicon wafer with the resistivity of 0.016 Ωcm or less at a high recovery rate. Therefore, in the automated automatic evaluation system, it is possible to evaluate metal contamination of the silicon wafer that is an evaluation target with high reliability.

[Manufacturing Method]

One aspect of the present invention relates to a method of manufacturing a boron-doped p-type silicon wafer including manufacturing the boron-doped p-type silicon wafer for process evaluation with the resistivity of 0.016 Ωcm or less in a process of manufacturing the boron-doped p-type silicon wafer, evaluating the presence, degree, or presence and degree of metal contamination of the boron-doped p-type silicon wafer for process evaluation according to the above metal contamination evaluation method, and determining the necessity of process management of the manufacturing process based on a result of evaluation, and manufacturing a boron-doped p-type silicon wafer for shipping as a product after process management when it is determined that process management is necessary or without process management when it is determined that process management is unnecessary.

Metal contamination of the silicon wafer can be generated due to the manufacturing process. In the above manufacturing method, metal contamination of a silicon wafer for process evaluation is evaluated according to the metal contamination evaluation method of one aspect of the present invention described above, and based on the evaluation results, the presence and/or degree of metal contamination in the manufacturing process in which the silicon wafer for process evaluation is manufactured is determined. As a result of the determination, when it is determined that process management for reducing metal contamination is necessary, the process management for reducing metal contamination is performed, and it is possible to stably perform mass production of silicon wafers with reduced metal contamination in the manufacturing process after process management. In addition, as a result of the determination, in the manufacturing process in which it is determined that process management is unnecessary, it is possible to continuously and stably perform mass production of silicon wafers with reduced metal contamination without performing process management for reducing metal contamination. Although the resistivity of the boron-doped p-type silicon wafer for process evaluation used for evaluation in the manufacturing process is 0.016 Ωcm or less, the resistivity of the boron-doped p-type silicon wafer manufactured in the above manufacturing process may be 0.016 Ωcm or less or more than 0.016 Ωcm.

The manufacturing process can be a manufacturing process known as a process of manufacturing a boron-doped p-type silicon wafer and is not particularly limited. Examples thereof include a manufacturing process in which various grinding and/or polishing treatments are performed on a boron-doped p-type silicon wafer cut out from a silicon single crystal ingot to manufacture a polished wafer and a process of manufacturing an annealed wafer including an annealing treatment. The process management performed in the process of manufacturing a silicon wafer can be performed to reduce metal contamination, and examples thereof include replacement, washing, and repair of members, pipes, and devices included in the manufacturing process, replacement and increasing the purity of a chemical solution used in the manufacturing process, and increasing the purity of a processing gas.

For other details of the above manufacturing method, known techniques related to manufacturing a boron-doped p-type silicon wafer can be applied.

EXAMPLES

Hereinafter, the present invention will be described in more detail with reference to examples. However, the present invention is not limited to embodiments shown in examples. Operations described below were performed at room temperature (20° C. to 25° C.) and under atmospheric pressure unless otherwise specified. In addition, % shown below is mass %.

In addition, the following etching test was performed using a chamber shown in FIG. 1 in Document 1 (WO2014/129246). In this chamber, an etching gas preparation chamber was provided on a gas phase decomposition chamber, both chambers communicated with each other in an air-permeable manner, and the gas phase decomposition chamber included an exhaust pipe through which at least some of the etching gas in contact with the surface of the silicon wafer was able be discharged to the outside of the chamber.

[Etching Test 1]

A plurality of boron-doped p-type silicon wafers (with a diameter of 300 mm and a resistivity of 0.016 Ωcm) manufactured in the same manufacturing process were prepared, and the wafers were etched under conditions in which flow rates of the ozone-containing gas were different. The etching was performed by the following method, and during etching, chamber temperatures in the gas phase decomposition chamber and the etching gas preparation chamber were maintained at 23° C. by a temperature control unit.

First, etching target wafers were introduced into the gas phase decomposition chamber.

The ozone-containing gas and the hydrofluoric acid mist were introduced into the etching gas preparation chamber. Specifically, regarding the ozone-containing gas, a 0.7 mass % ozone-containing gas was introduced continuously in a continual manner into the etching gas preparation chamber at a flow rate of level 5 shown in Table 1. Regarding the hydrofluoric acid mist, nitrogen gas as a carrier gas was caused to flow (flow rate: 700 sccm), into a negative pressure suction type nebulizer (hydrofluoric acid suction rate: 300 μl/min to 400 μl/min), hydrofluoric acid was atomized, and the hydrofluoric acid mist was continuously sprayed into the etching gas preparation chamber in a continual manner. Regarding the hydrofluoric acid used for preparing the hydrofluoric acid mist, hydrofluoric acid with a hydrofluoric acid concentration of 44% was used. Therefore, the ozone-containing gas and the hydrofluoric acid mist were mixed in the etching gas preparation chamber, the mixture was supplied to the gas phase decomposition chamber, and etching was performed. The etching was performed for 2 hours.

Then, the silicon wafer was removed from the gas phase decomposition chamber, and transferred to a heating stage, and heated on the heating stage for about 5 minutes (wafer surface temperature of about 100° C.). According to this heating, it was possible to remove water on the surface of the wafer after etching and/or easily decomposable substances.

The silicon wafer after heating was transferred to a scan stage, and 1,000 μl of a recovery liquid (acid aqueous solution (HF concentration 2%, $H_2O_2$ concentration 2%)) was added dropwise to the surface of the wafer on the scan stage, and while the droplets were maintained at the tip of the scan nozzle, the scan nozzle was moved at a rate 2 mm/s, and the droplets were scanned on the entire surface of the wafer. Then, the droplets at the nozzle tip were sucked and recovered through the scan nozzle. Liquid amounts of the recovery liquids that were recovered are shown in Table 1.

TABLE 1

| | Flow rate of ozone-containing gas [sccm] | Recovery amount of recovery liquid [μl] |
|---|---|---|
| Comparative Example 1 | 1000 | 334 |
| Comparative Example 2 | 2000 | 341 |
| Example 1 | 3000 | 950 |
| Example 2 | 4000 | 957 |
| Example 3 | 5000 | 990 |

[Etching Test 2]

An etching test was performed in the same manner as in the Etching test 1 except that a plurality of boron-doped p-type silicon wafers (with a diameter of 300 mm and a resistivity of 0.010 Ωcm) manufactured in the same manufacturing process were etched. Liquid amounts of the recovery liquids recovered from the surface of the wafer after etching are shown in Table 2.

TABLE 2

| | Flow rate of ozone-containing gas [sccm] | Recovery amount of recovery liquid [μl] |
|---|---|---|
| Comparative Example 3 | 1000 | 335 |
| Example 4 | 3000 | 956 |
| Example 5 | 4000 | 957 |
| Example 6 | 5000 | 931 |

[Etching Test 3 (Reference Test)]

An etching test was performed in the same manner as in the Etching test 1 except that a plurality of boron-doped p-type silicon wafers (with a diameter 300 mm and a resistivity of 10 Ωcm) manufactured in the same manufacturing process were etched. Liquid amounts of the recovery liquids recovered from the surface of the wafer after etching are shown in Table 3.

TABLE 3

|  | Flow rate of ozone-containing gas [sccm] | Recovery amount of recovery liquid [μl] |
| --- | --- | --- |
| Reference Example 1 | 1000 | 1002 |
| Reference Example 2 | 2000 | 1012 |
| Reference Example 3 | 3000 | 1011 |
| Reference Example 4 | 4000 | 1023 |
| Reference Example 5 | 5000 | 1013 |

[Etching Test 4]

A plurality of boron-doped p-type silicon wafers (with a diameter of 300 mm and a resistivity of 0.016 Ωcm) manufactured in the same manufacturing process were prepared, and the wafers were etched under conditions in which hydrofluoric acid concentrations of hydrofluoric acid used for preparing the hydrofluoric acid mist were different. The etching was performed by the following method, and during etching, chamber temperatures in the gas phase decomposition chamber and the etching gas preparation chamber were maintained at 23° C. by a temperature control unit.

First, wafers as etching targets were introduced into the gas phase decomposition chamber.

The ozone-containing gas and the hydrofluoric acid mist were introduced into the etching gas preparation chamber. Specifically, regarding the ozone-containing gas, a 0.7 mass % ozone-containing gas was introduced continuously in a continual manner into the etching gas preparation chamber at a flow rate of 3,000 sccm. Regarding the hydrofluoric acid mist, nitrogen gas as a carrier gas was caused to flow (flow rate: 700 sccm), into a negative pressure suction type nebulizer (hydrofluoric acid suction rate: 300 μl/min to 400 μl/min), hydrofluoric acid was atomized, and the hydrofluoric acid mist was continuously sprayed into the etching gas preparation chamber in a continual manner. Regarding the hydrofluoric acid used for preparing the hydrofluoric acid mist, hydrofluoric acid with a hydrofluoric acid concentration of level 5 shown in Table 4 was used. Therefore, the ozone-containing gas and the hydrofluoric acid mist were mixed in the etching gas preparation chamber, the mixture was supplied to the gas phase decomposition chamber, and etching was performed. The etching was performed for 2 hours.

Then, the silicon wafer was removed from the gas phase decomposition chamber, and transferred to a heating stage, and heated on the heating stage for about 5 minutes (wafer surface temperature of about 100° C.). According to this heating, it was possible to remove water on the surface of the wafer after etching and/or easily decomposable substances.

The silicon wafer after heating was transferred to a scan stage, and 1,000 μl of a recovery liquid (acid aqueous solution (HF concentration 2%, H$_2$O$_2$ concentration 2%)) was added dropwise to the surface of the wafer on the scan stage, and while the droplets were maintained at the tip of the scan nozzle, the scan nozzle was moved at a rate 2 mm/s, and the droplets were scanned on the entire surface of the wafer. Then, the droplets at the nozzle tip were sucked and recovered through the scan nozzle. Liquid amounts of the recovery liquids that were recovered are shown in Table 4.

TABLE 4

|  | Concentration of hydrofluoric acid [%] | Recovery amount of recovery liquid [μl] |
| --- | --- | --- |
| Comparative Example 4 | 38 | 342 |
| Example 7 | 41 | 955 |
| Example 8 | 44 | 950 |
| Example 9 | 47 | 1002 |
| Example 10 | 50 | 1025 |

[Etching Test 5]

An etching test was performed in the same manner as in the Etching test 4 except that a plurality of boron-doped p-type silicon wafers (with a diameter of 300 mm and a resistivity of 0.010 Ωcm) manufactured in the same manufacturing process were etched. Liquid amounts of the recovery liquids recovered from the surface of the wafer after etching are shown in Table 5.

TABLE 5

|  | Concentration of hydrofluoric acid [%] | Recovery amount of recovery liquid [μl] |
| --- | --- | --- |
| Comparative Example 5 | 38 | 335 |
| Example 11 | 41 | 946 |
| Example 12 | 44 | 956 |
| Example 13 | 47 | 957 |
| Example 14 | 50 | 931 |

[Etching Test 6 (Reference Test)]

An etching test was performed in the same manner as in the Etching test 4 except that a plurality of boron-doped p-type silicon wafers (with a diameter 300 mm and a resistivity of 10 Ωcm) manufactured in the same manufacturing process were etched. Liquid amounts of the recovery liquids recovered from the surface of the wafer after etching are shown in Table 6.

TABLE 6

|  | Concentration of hydrofluoric acid [%] | Recovery amount of recovery liquid [μl] |
| --- | --- | --- |
| Reference Example 6 | 38 | 1022 |
| Reference Example 7 | 41 | 1009 |
| Reference Example 8 | 44 | 1013 |
| Reference Example 9 | 47 | 1015 |
| Reference Example 10 | 50 | 1011 |

Comparing the results of the Etching tests 1, 2, 4, and 5 with the results of the Etching tests 3 and 6 (reference tests), it was confirmed that, in the low-resistance boron-doped p-type silicon wafer with the resistivity of 0.016 Ωcm or less, a phenomenon, in which the recovery rate of the recovery liquid after etching was low, occurred.

In addition, comparing examples with comparative examples in Tables 1, 2, 4, and 5, it was confirmed that such a decrease in the recovery rate of the recovery liquid was able to be minimized when the flow rate of the ozone-containing gas for preparing an etching gas was set to 3,000 sccm or more and the hydrofluoric acid concentration of the hydrofluoric acid was set to 41% or more. The reason why the recovery amounts of the recovery liquids in Table 3 and Table 6 slightly exceeded the amount of the recovery liquid added dropwise to the surface of the wafer was speculated that a small amount of by-products generated due to the gas phase decomposition reaction was also recovered in the recovery liquid.

[Metal contaminant evaluation test]

A contaminated wafer with a known metal contaminant amount was prepared by the following method.

1 ml of a contaminated liquid (0.2% nitric acid aqueous solution) in which respective concentrations of Fe, Ni, and Cu each were adjusted to 1 ppb was added dropwise to the surfaces of a plurality of boron-doped p-type silicon wafers (with a diameter of 300 mm and a resistivity of 0.016 Ωcm) manufactured in the same manufacturing process, and natural drying was then performed in a clean bench.

A plurality of boron-doped p-type silicon wafers (with a diameter of 300 mm and a resistivity of 0.010 Ωcm or 10 Ωcm manufactured in the same manufacturing process were similarly treated to prepare contaminated wafers.

The contaminated wafers were etched in the same manner as in the Etching test 4 and a surface layer area on the side of the surface contaminated with a contaminated liquid was subjected to gas phase decomposition except that the hydrofluoric acid concentration of the hydrofluoric acid used for preparing the hydrofluoric acid mist was set to 50% or 38%, and additionally, scanning and recovery of the recovery liquid were performed in the same manner as in the Etching test 4. The recovery liquid that was recovered was introduced into ICP-MS and various metal components were quantitatively analyzed. The above known contaminant amount was set as 100%, and the recovery rate of each metal component that was quantitatively analyzed was calculated. The results are shown in Table 7. In Table 7, there is a value in which the recovery rate is slightly higher than 100%, which is speculated to be due to measurement errors caused by the ICP-MS device used for quantitative analysis.

0.016 Ωcm or less was able be suppressed as shown in Table 7 because the recovery liquid was able to be recovered at a high recovery rate. In this manner, metal components were recovered from the wafer after etching at a high recovery rate, the metal contamination were evaluated, process management was performed using the evaluation results, and thus it was possible to stably supply silicon wafers with reduced metal contamination and high quality.

One aspect of the present invention is beneficial in the technical field of silicon wafers that can be used as semiconductor substrates.

The invention claimed is:

1. A method of etching a boron-doped p-type silicon wafer, comprising:
   preparing an etching gas by introducing an ozone-containing gas and hydrofluoric acid mist into a chamber and mixing them; and
   performing gas phase decomposition of a surface layer area of a boron-doped p-type silicon wafer with a resistivity of 0.016 Ωcm or less by bringing the etching gas into contact with a surface of the boron-doped p-type silicon wafer; and further comprising:
   introducing the ozone-containing gas into the chamber at a flow rate of 3,000 sccm or more; and
   preparing the hydrofluoric acid mist by atomizing hydrofluoric acid with a hydrofluoric acid concentration of 41 mass % or more.

2. The method of etching a boron-doped p-type silicon wafer according to claim 1,
   wherein an ozone concentration of the ozone-containing gas is in a range of 0.5 mass % to 3.5 mass %.

3. The method of etching a boron-doped p-type silicon wafer according to claim 1, comprising preparing the hydrofluoric acid mist by atomizing hydrofluoric acid with a carrier gas at a flow rate of 700 sccm or more and 1,300 sccm or less.

TABLE 7

| | Etching gas | | Fe | | Ni | | Cu | |
| --- | --- | --- | --- | --- | --- | --- | --- | --- |
| Contaminated wafer | Flow rate of ozone-containing gas | Concentration of hydrofluoric acid | Analysis result [ppb] | Recovery rate [%] | Analysis result [ppb] | Recovery rate [%] | Analysis result [ppb] | Recovery rate [%] |
| Resistivity 0.010 Ωcm | | | 0.432 | 43% | 0.431 | 43% | 0.399 | 40% |
| Resistivity 0.016 Ωcm | 3000 sccm | 38% | 0.363 | 36% | 0.366 | 37% | 0.321 | 32% |
| Resistivity 10 Ωcm | | | 0.998 | 100% | 1.03 | 103% | 0.902 | 90% |
| Resistivity 0.010 Ωcm | | | 0.956 | 96% | 0.918 | 92% | 0.908 | 91% |
| Resistivity 0.016 Ωcm | 3000 sccm | 50% | 1.01 | 101% | 0.998 | 100% | 0.933 | 93% |
| Resistivity 10 Ωcm | | | 0.967 | 97% | 0.976 | 98% | 0.961 | 96% |

As described above, when the flow rate of the ozone-containing gas for preparing an etching gas was set to 3,000 sccm or more and the hydrofluoric acid concentration of the hydrofluoric acid was set to 41% or more, it was possible to recover the recovery liquid from the surface of the low-resistance boron-doped p-type silicon wafer with the resistivity of 0.016 Ωcm or less after etching at a high recovery rate. It is thought that a decrease in the recovery rate of metal components significantly occurring in the low-resistance boron-doped p-type silicon wafer with the resistivity of 4. The method of etching a boron-doped p-type silicon wafer according to claim 3, comprising introducing the carrier gas into a chamber separate from the chamber into which the ozone-containing gas and the hydrofluoric acid mist are introduced and performing the gas phase decomposition in the separate chamber.

5. A method of evaluating metal contamination of a boron-doped p-type silicon wafer,
   wherein a resistivity of the boron-doped p-type silicon wafer that is an evaluation target is 0.016 Ωcm or less, the method comprising:

etching the boron-doped p-type silicon wafer by the etching method according to claim 1;

scanning a recovery liquid on a surface of the boron-doped p-type silicon wafer after etching;

recovering the scanned recovery liquid from the surface of the boron-doped p-type silicon wafer; and analyzing metal components in the recovery liquid that are recovered.

6. A method of manufacturing a boron-doped p-type silicon wafer, comprising:

manufacturing the boron-doped p-type silicon wafer for process evaluation with a resistivity of 0.016 Ωcm or less in a process of manufacturing a boron-doped p-type silicon wafer;

evaluating presence, degree, or presence and degree of metal contamination in the boron-doped p-type silicon wafer for process evaluation by the metal contamination evaluation method according to claim 5; and determining necessity of process management of the manufacturing process based on a result of evaluation; and manufacturing a boron-doped p-type silicon wafer for shipping as a product after process management when it is determined that process management is necessary or without process management when it is determined that process management is unnecessary.

* * * * *